United States Patent [19]

Hall

[11] Patent Number: 5,411,511

[45] Date of Patent: May 2, 1995

[54] METHOD AND DEVICE FOR DETERMINING PLACEMENT OF KERATOTOMY INCISIONS

[76] Inventor: Gary W. Hall, 2501 N. 32nd St., Phoenix, Ariz. 85008

[21] Appl. No.: 151,273

[22] Filed: Nov. 12, 1993

[51] Int. Cl.⁶ .............................................. A61B 17/32
[52] U.S. Cl. .................. 606/166; 83/522.14; 606/170
[58] Field of Search ............... 606/166, 167, 170, 172; 83/522.11, 522.12, 522.14, 522.26

[56] References Cited

U.S. PATENT DOCUMENTS

| | | | |
|---|---|---|---|
| 4,178,820 | 12/1979 | Gerber | 83/13 |
| 4,200,015 | 4/1980 | Gerber | 83/22 |
| 4,543,867 | 10/1985 | Ichikawa | 83/522.14 |
| 4,637,393 | 1/1987 | Ray | 606/166 |
| 4,665,914 | 5/1987 | Tanne | 606/166 |
| 4,750,489 | 6/1988 | Berkman et al. | 606/166 |
| 4,943,296 | 7/1990 | Funakubo et al. | 606/166 |
| 5,222,967 | 6/1993 | Casebeer et al. | 606/166 |
| 5,308,355 | 5/1994 | Dybbs | 606/166 |

FOREIGN PATENT DOCUMENTS 1337045  9/1987  U.S.S.R. ............................ 606/167

OTHER PUBLICATIONS

"Introduction to Biomechanics of the Cornea" by Kurt A. Buzard, MD, FACS, Retractive & Corneal Surgery, vol. 8, Mar./Apr. 1992, pp. 127–138.

*Primary Examiner*—Stephen C. Pellegrino
*Assistant Examiner*—Nancy Mulcare
*Attorney, Agent, or Firm*—Cahill, Sutton & Thomas

[57] ABSTRACT

A keratotomy incision is formed in a cornea manipulating an RK knife so that its blade extends a preselected depth into a preselected point on the cornea. Sufficient force is applied by a surgeon's fingers to the knife to advance its blade in a preselected direction. Advancement of the blade is halted when resistance of the cornea against the blade exceeds a certain level. A signal representative of the resistance is produced by a strain gauge or transducer in or on the knife. The level of the resistance is indicated on a display or audibly in response to the signal.

13 Claims, 3 Drawing Sheets

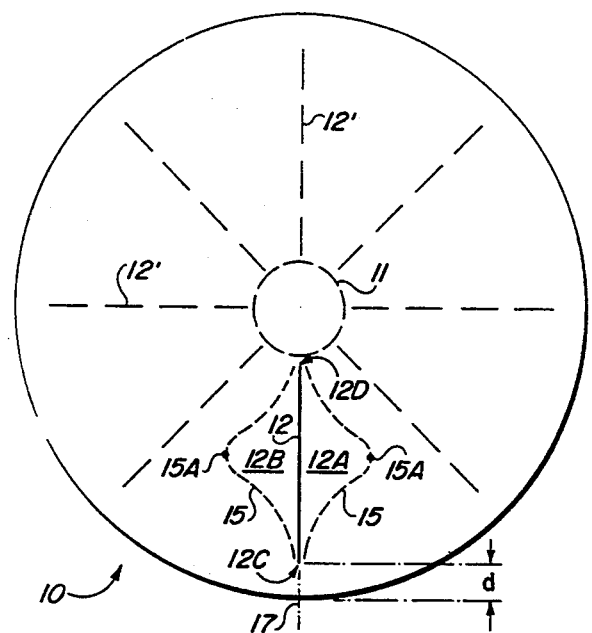
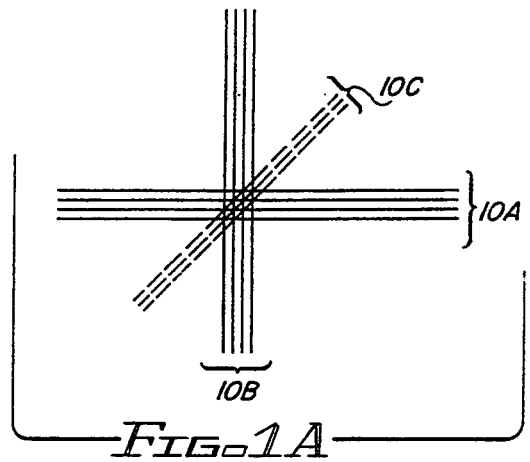
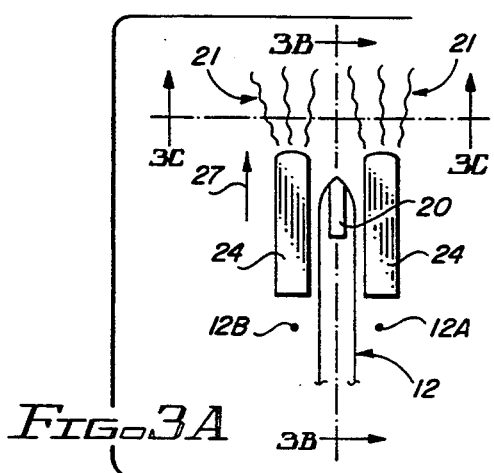
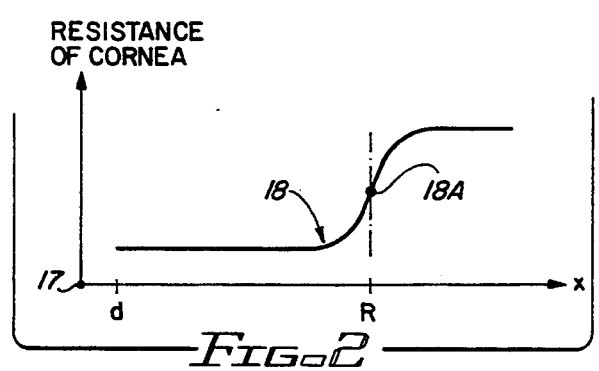
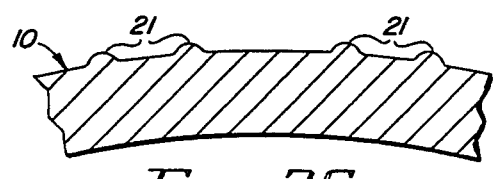
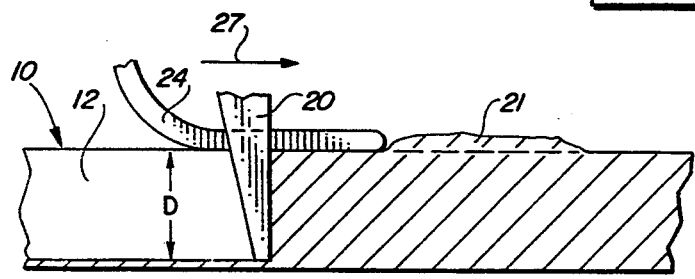
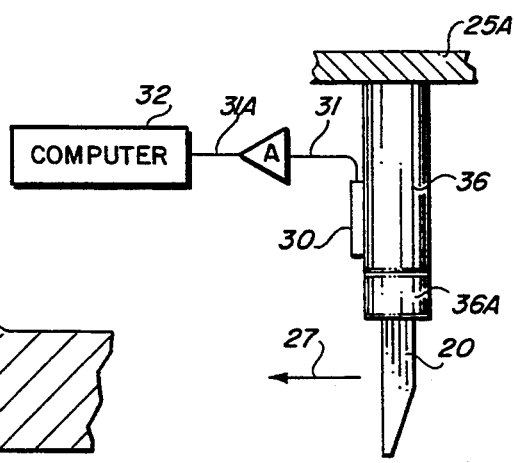

METHOD AND DEVICE FOR DETERMINING PLACEMENT OF KERATOTOMY INCISIONS

BACKGROUND OF THE INVENTION

The invention relates to a method of determining the extent of a keratotomy incision by determining a point of increased resistance against blade advancement of an RK knife as it makes the incision. The incision is stopped when a critical level of resistance is detected. The resulting incision length optimally corrects the patients vision.

Ophthalmologists usually use "optical zone markers" to determine the length of a keratotomy incision. A radial RK incision typically begins approximately a millimeter from the outer edge of the cornea. The blade of an RK knife is moved radially inward toward an "optical zone marker" (which is a shallow indentation previously made in the epithelium by the surgeon around a central area of the cornea by pressing a stainless steel device known as a zone marker against the central cornea). An astigmatic keratotomy (AK) is performed by making the incision(s) tangential to the steepest radial curvature of the cornea in a linear or curvilinear fashion at a predetermined optical zone. The size of the optical zone markers usually is made according to nomograms or empirical formulas based on age, sex, degree of correction needed, thickness, curvature, and/or diameter of the cornea. However, such nomograms and empirical formulas are based on averages for a large number of patients, and are not necessarily accurate for a particular patient if his or her eye has "non-average" material properties.

There is an unmet need for a technique and device for optimizing lengths of keratotomy incisions based primarily on the material properties of the cornea and its behavior in response to such incisions.

SUMMARY OF THE INVENTION

Accordingly, it is an object of the invention to provide a method for placement of keratotomy incisions (to correct refractive errors) based primarily on the material properties of the cornea.

It is another object of the invention to provide a radial keratotomy knife adapted to aid in optimal placement of each incision for correction of refractive errors, including myopia, astigmatism, hyperopia and/or combinations thereof.

It is another object of the invention to provide a way of optimally reducing stress and strain in the cornea to improve vision.

Briefly described, and in accordance with one embodiment thereof, the invention provides a method of making an incision in a cornea by manipulating an RK (radial keratotomy) knife so that its blade extends a preselected distance into the cornea at a preselected point thereof. Sufficient force is applied to the RK knife to advance the blade in a preselected direction. Movement of the blade is halted to complete the incision when resistance of the cornea against the blade exceeds a critical level. In one embodiment of the invention a surgeon uses an RK knife with sufficiently low friction that the surgeon is able to feel the critical resistance and stop the incision accordingly. In another embodiment of the invention, the amount of force applied by the surgeon's fingers to a body of the RK knife produces a signal representative of the force. The signal indicates the level of resistance of the cornea against a leading edge of the blade. The level of the resistance is displayed on a computer screen and/or is audibly indicated. In another embodiment the blade is supported on an elastic member. The counterforce produced by resistance of the cornea against the leading edge of the blade is indicated by producing a signal representing the amount of elastic deformation of the elastic member.

BRIEF DESCRIPTION OF THE DRAWINGS

FIG. 1 is a plan view diagram useful in explaining the theory of the present invention.

FIG. 1A is a diagram of a cross section of a corneal incision, and is useful in describing the theory of the present invention.

FIG. 2 is a diagram of resistance of the cornea against a leading edge of a radial keratotomy blade, while making an incision.

FIG. 3A is a plan view illustrating a phenomena causing increased resistance to advancement of the radial keratotomy knife as stress and strain in the cornea is reduced along the sides of the incision.

FIG. 3B is a sectional view taken along section line 3B—3B of FIG. 3A.

FIG. 3C is a sectional view taken along section line 3C—3C of FIG. 3A.

FIG. 8 is a perspective view of another embodiment of a radial keratotomy knife adapted to sense resistance imparted to the blade as it advances to form a corneal incision.

DETAILED DESCRIPTION OF THE PREFERRED EMBODIMENTS

Figure 4:
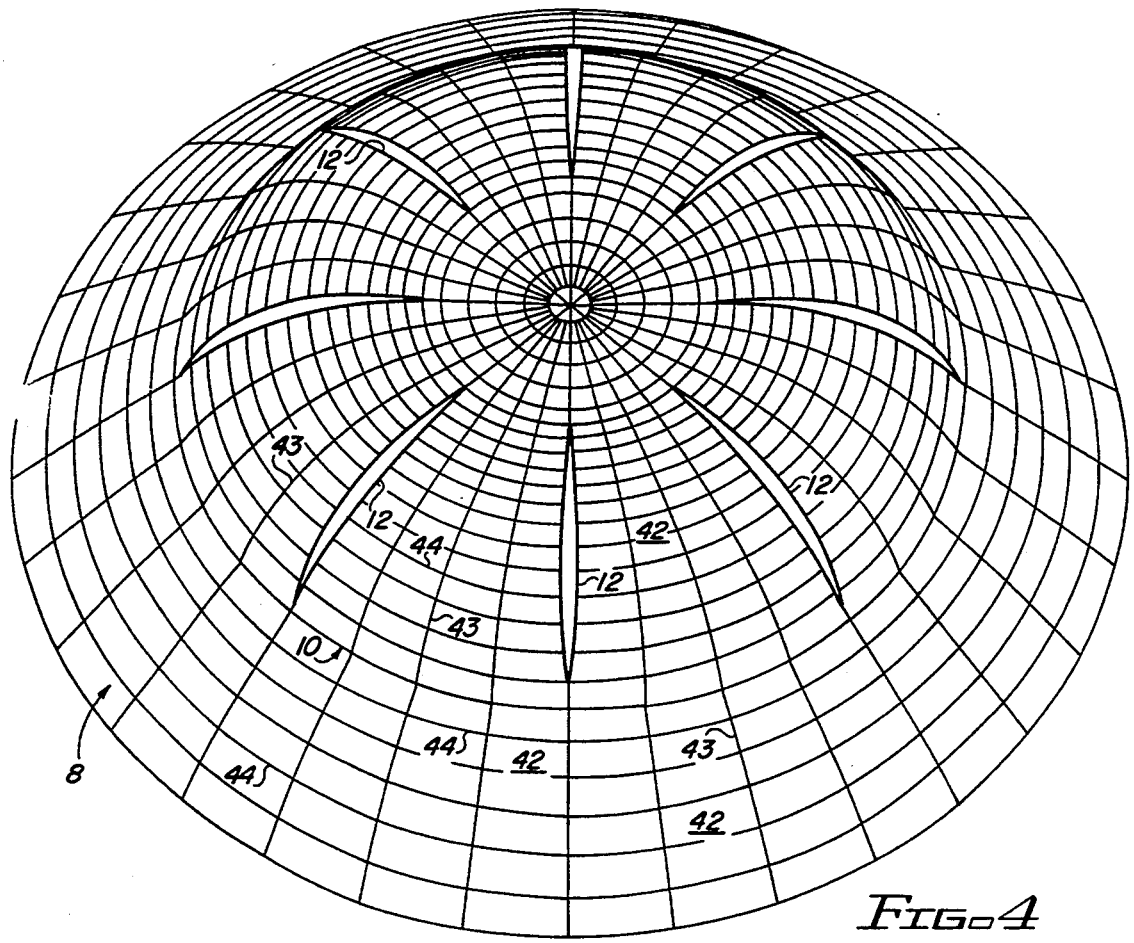
FIG. 4 is a perspective view of a finite element analysis model of an eye having a plurality of RK incisions in the cornea.

As I performed various procedures to correct myopia and/or astigmatism through incisional keratotomy using a relatively new, exceptionally thin blade, I realized that the blade could be advanced very easily through the corneal stroma, compared to advancement of the thicker, more conventional blades I had previously used. Such previous blades had pointed tips, and were approximately 150 micrometers thick. The new blade was a "Thornton type", 80 micrometers in thickness, with a squared tip. The trailing edge of the squared tip was inclined 18 degrees relative to the leading edge.

To my surprise, for each advancement of the blade to form a keratotomy incision a "resistance point" was reached in the cornea. I realized that the blade would not pass beyond the resistance point without considerably increased exertion.

I continued to experiment, and discovered that even within the same cornea some of the resistance points (which I found to occur in both astigmatic and radial incisions) were located before preestablished optical zone markers, and other such resistance points were located beyond the optical zone marker. Using these resistance points, rather than the optical zone markers, as a guide for determining the incision lengths, I discovered that different length incisions frequently would occur on the same cornea, some shorter than indicated by the optical zone marker and others longer. I also noticed that the new Thornton type blade typically could be advanced more easily through the stroma of patients who had the higher degree of nearsightedness and astigmatism.

The graph of FIG. 2 qualitatively illustrates the amount of force applied to an RK knife as the incision is being made in the direction x. Numeral 17 designates the outer edge of the cornea 10, and the solid line 18 indicates the amount of force being applied to advance the blade. At point R the force required to advance the blade increases abruptly, as indicated by 18A. My experimental results indicate that this point corresponds to the optimum correction of a myopic or astigmatic condition.

Initially, I was unable to provide a plausible explanation for the resistance points. I considered various possible effects of blade tilt, bunching of the epithelium against the RK knife, compaction of collagen by establishment of optical zone markers, and cornea surface irregularity as causes of the resistance points. I eventually ruled these out as causative factors as a result of my further observations. I asked a few other ophthalmologists if they had recognized such resistance points, but none could identify with what I was saying.

I continued to experiment with the technique of stopping the incision at the resistance points rather than at the optical zone markers because I discovered that the new technique seemed to be producing better correction, with far fewer significant overcorrections or undercorrections than when the optical zone markers based on empirical nomograms are strictly adhered to to determine each incision length.

My attempts to develop a theory to explain the occurrence of the above resistive points are partly based on information regarding stress/strain relationships computed for a cornea with RK incisions therein using a finite element analysis (FEA) model. FIG. 4 shows a diagram of the surface of cornea 10. (The terms "stress" and "strain" have the following common meanings. The stress is equal to the amount of load force applied to a bar of material divided by the cross sectional area thereof. The strain is the change in length or deformation of the bar due to the load force divided by the "original" length of the bar. Young's modulus is the ratio of the stress to the strain. See "Introduction to Biomechanics of the Cornea" by Kurt A. Buzard, M.D. published in "Refractive & Corneal Surgery", Volume 8, March/April 1992, page 127.) Numeral 42 designates the finite elements of the model, each of which is bounded by adjacent "radial" lines 43 and two adjacent "equatorial" lines 44. Eight RK incisions 12 have been included in the illustrated model. The FEA model used to generate FIG. 4 was found to accurately represent a patient's eye having the same material properties as those used in the model.

Figure 5:
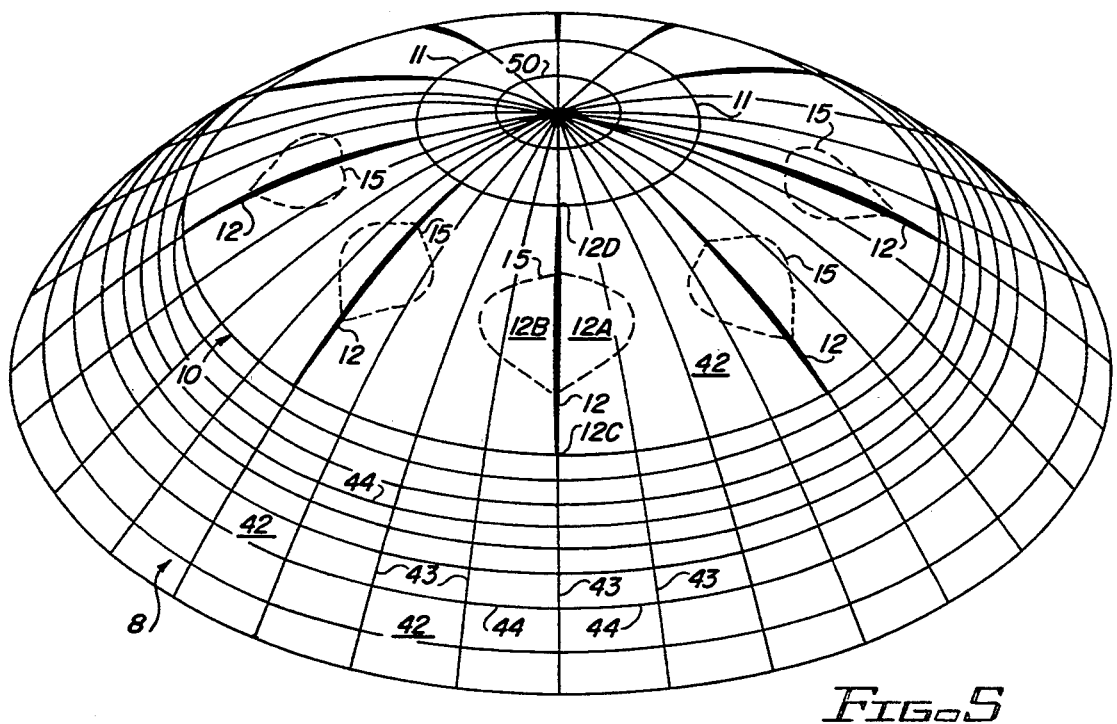
FIG. 5 is a perspective view similar to FIG. 6 with areas of different levels of stress and strain indicated thereon.

FIG. 5 shows a scale diagram of the surface of an eye as traced from a display computed by the same FEA model as FIG. 4, and further indicates the computed stress/strain in the epithelium throughout the sclera and cornea 10. The display referred to was a color display, the colors in various areas indicating the computed stress/strain level thereat. The highest levels of stress/strain were indicated by red color within the central area 50. Lower levels were indicated by a yellow band between area 50 and the zone indicated by 11. The band between the outer boundary of cornea 10 and zone 11 had several lower stress/strain levels indicated by several shades of blue, respectively. The lowest levels of stress/strain occurred in the material in the regions bounded by dotted line 15 along the central side portions 12A and 12B of modeled incisions 12 (as also indicated above in FIG. 1). In the original computer display, regions 15 appeared as a very dark blue color. The lowest stress/strain regions 15 were included in a generally annular low stress/strain band shown in the original display as a different, lighter shade of blue. The sclera 8 appeared as a yellow band, with high levels of computed stress in the surface material represented by the corresponding FEA elements 42.

FIG. 5 thus shows that the lowest stress/strain points occur alongside of the incision 12 and the highest stress/strain points occur at the front end of the incision being formed by the leading edge of an advancing blade 20.

Figure 6:
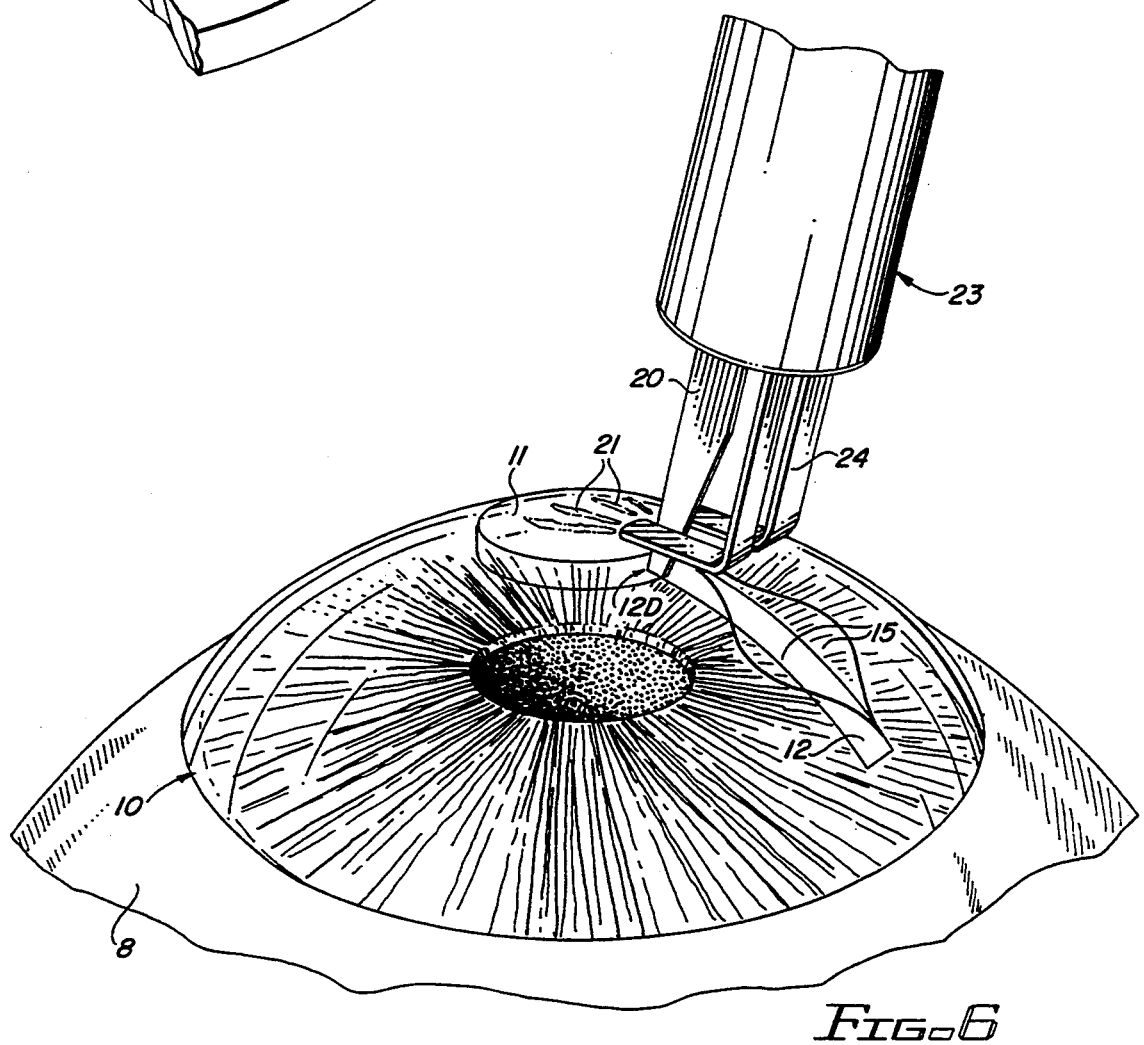
FIG. 6 is a perspective view illustrating the making of a keratotomy incision, with areas of high and low stress and strain in the cornea indicated, and "bunching" or folding to form stria in the epithelium beyond the RK knife.

I observed that folds or stria 21 appear on the surface of the epithelium just ahead of the leading edge of blade 20 and the feet 24 of the RK knife just as the sharp increase in resistance to blade 20 occurred. The cross sectional view shown in FIG. 3C along section lines 3C—3C of FIG. 3A illustrates the stria 21, and FIG. 6 perhaps best illustrates the appearance of the stria 21.

The stress/strain information in FIG. 5 led me to recognize that as the stress/strain at the inner tip 12D of the incision increases to a critical level, the blade 20 would no longer easily advance through the epithelium. (The increase in force is definitely made more noticeable when mechanically thin diamond blades are used, because they create less friction.) The stress/strain distribution computed using the finite element analysis model shows minimum stress/strain in the cornea material along the sides 12A and 12B of incision 12 (FIG. 3A). The highest stress/strain point probably occurs just ahead of the leading edge of blade 20.

As indicated in FIG. 1A, the stroma of cornea 10 is comprised of a number of parallel layers of lamellae that includes bundles of parallel collagen fibers. The bundles of the various layers are approximately 10 microns thick, and run in various directions. In FIG. 1A, numeral 10A designates a bundle of lamellae fibers in one layer, running in a direction parallel to the page. Numeral 10B designates bundles in an adjoining layer running in a direction perpendicular to bundle 10A, and numeral 10C designates bundles of lamellae in yet another layer running obliquely to the directions of fibers 10A and 10B. There are enough lamellae fibers running in different directions at any point in the cornea that an incision being made in virtually any direction will experience the "bunching" and stress/strain redistribution that causes the stria 21 illustrated in FIGS. 3A, 3C, and 6. Apparently, such bunching occurs as a result of both the relaxation of the stress/strain along the sides 12A and 12B of the incision 12, and the increase in stress/strain and consequent increase in the density or compactness of uncut lamellae in front of the blade as the critical stress/strain level is achieved. However, I do not fully understand how or why this phenomenon occurs.

My experiments and the development of my theory to date seem to indicate that when the stress/strain relationships in the cornea reach an optimum "equilibrium" or "low" point, the resistance force reaches the above mentioned critical level, beyond which "excessive" force is required to continue advancing the RK knife. If the RK knife is advanced beyond that point, possibly a loss of "equilibrium" of the stress/strain relationships occurs, and more stress/strain is introduced into the cornea.

The most unexpected result observed from my experiments is that the above mentioned critical resistance points seem to correspond with optimal visual correction, i.e., the point at which emmetropia is achieved. There appears to be a "natural point", i.e., an equilibrium point, which the cornea "wants" to reach. For "ametropia" or abnormal refractive conditions, the stress/strain in the cornea appears to be abnormally high. Stated differently, the results of my experiments to date have led me to believe that the condition of emmetropia may be closely related to achieving of the lowest overall possible stress/strain in a particular cornea, and that the degree of ametropia is proportional to the degree of abnormal stress/strain leading to the myopia or astigmatic condition being corrected.

If the incisions are stopped at the critical resistance points, then optimum vision should be achieved for the particular patient. This appears to be the case because the incisions are being made as a function of the material behavior of the present cornea, rather than being based on average empirical formulas or nomograms. I now use the conventional optical zone markers merely as a general indicator of the approximate desired incision length, but I rely on the critical resistance point to actually determine the length of each incision.

The reliability of the above described technique makes it possible to avoid the usual tendency of a surgeon to make keratotomy incisions as deep as possible, and therefore reduces the occurrences of micro-perforations, in addition to reducing the occurrence of significant overcorrection or undercorrection of the cornea, and therefore reduces the need for subsequent "extending" of earlier incisions. Furthermore, as each incision is made, the critical resistance point automatically incorporates not only the material properties of that cornea, but also the effects of previously placed incisions and possibly other factors that affect stress/strain relationships in that eye, such as intraocular pressure.

Although the results of my experiments indicate that I have been able to "feel" the resistance point with reasonable accuracy to optimally terminate each incision, it would be highly desirable to provide an RK knife that includes a way of automatically sensing the increased resistance level at which the present incision should be stopped.

Figure 7:
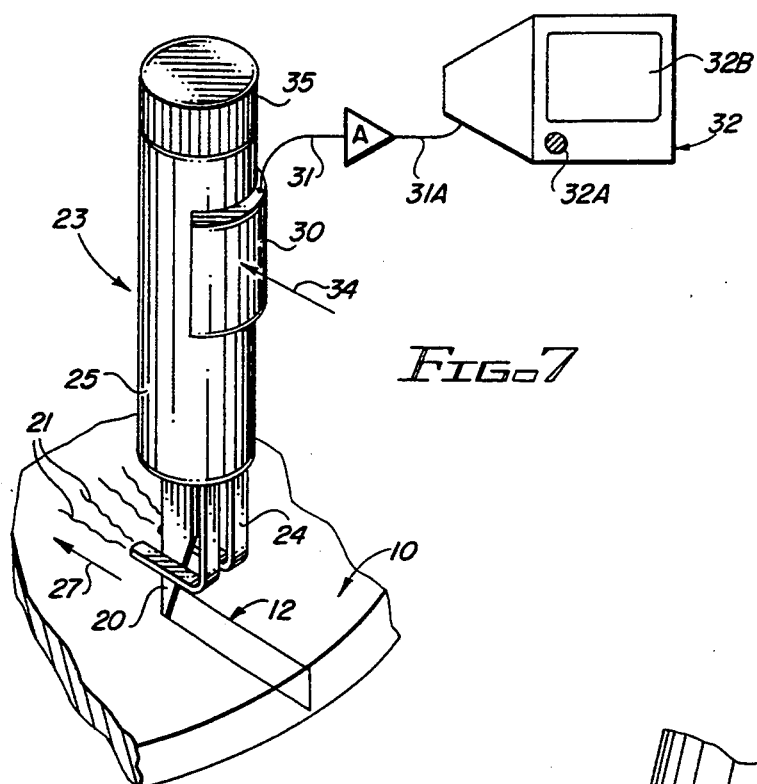
FIG. 7 is a perspective view of one embodiment of a radial keratotomy knife adapted to sense resistance to advancement of the knife making a radial keratotomy incision.

FIG. 7 shows one approach to designing such an RK knife. RK knife 23 includes a conventional body 25 and micrometer adjustment 35 that adjusts the depth of the lower tip of blade 20 relative to the bottom surfaces of each foot 24 (which slides along the cornea surface as the incision is made). Arrow 27 indicates the direction of advancing blade 20 as the incision 12 is being formed. A pressure or strain measuring device 30 is affixed to or incorporated in the surface of the body 25 of RK knife 20, and produces signals on conductors 31 indicating how much pressure the surgeon is applying to advance blade 20 through the cornea. That information is communicated, either by wires 31 and an amplifier or by an RF or infrared communication coupling, to a computing device 32 which analyzes that information and produces a graphic and/or audible output immediately indicating to the surgeon when the critical resistance point has been reached.

FIG. 8 discloses another embodiment, in which the blade 20 is mounted on the end of an elastic elongated support 36, the upper portion of which is anchored firmly in the upper portion of the RK knife body (not shown). As pressure is applied to the body of the RK knife by the fingers of the surgeon, the elongated elastic member 36 flexes by an amount proportional to the resistance that the cornea exerts against the leading edge of blade 20. A strain gauge 30 is adhesively or otherwise attached to the surface of elastic member 36 and generates a corresponding electric signal 31 that indicates the amount of flexing and hence the amount of resistance the cornea applies against advancement of blade 20. Signal 31 may be applied to an input of an amplifier included within or external to body 25. The amplifier output is coupled, either by means of conductors or a wireless communication link, to computing device 32. Computing device 32 generates graphic and/or audible information that indicates the amount of resistance of collagen at the front edge of the incision 12 against the leading edge of blade 20.

While the invention has been described with reference to several particular embodiments thereof, those skilled in the art will be able to make the various modifications to the described embodiments of the invention without departing from the true spirit and scope of the invention. It is intended that all combinations of elements and steps which perform substantially the same function in substantially the same way to achieve the same result are within the scope of the invention.

What is claimed is:

1. A method of making an incision in a cornea, comprising the steps of:
   (a) manipulating an RK knife so that a blade thereof extends a particular depth into the cornea at a particular point on the cornea;
   (b) applying sufficient force to the RK knife to advance the blade in a particular direction; and
   (c) halting movement of the blade in the particular direction when resistance of the cornea against a leading edge of the blade exceeds a particular level.

2. The method of claim 1 including detecting a force applied to a body of the RK knife, producing an electrical signal in response to the force, the electrical signal being representative of the amount of the force, and indicating the level of resistance of the cornea against the leading edge of the blade in response to the electrical signal.

3. The method of claim 2 including graphically indicating the level of the resistance on a computer screen in response to the electrical signal.

4. The method of claim 2 including audibly indicating the level of the resistance in response to the electrical signal.

5. The method of claim 1 including supporting the blade on an elastic member and detecting force on the leading edge of the blade by producing the electrical signal to represent an amount of elastic deformation of the elastic member resulting from the force on the leading edge of the blade and indicating the level of resistance of the cornea against the leading edge of the blade in response to the electrical signal.

6. A method of making an incision in a cornea, comprising the steps of:

(a) manipulating an RK knife so that a blade thereof extends a particular depth into the cornea at a particular point on the cornea;
(b) applying sufficient force to the RK knife to advance the blade in a particular direction; and
(c) halting movement of the blade in the particular direction when stria are observed on a surface of the cornea immediately ahead of the blade.

7. A method of making an incision in a cornea, comprising the steps of:
(a) manipulating an RK knife so that a blade thereof extends a particular depth into the cornea at a particular point on the cornea;
(b) applying a force to the RK knife sufficient to advance the blade in a particular direction along the cornea to form the incision;
(c) producing an electrical signal in response to the force, the electrical signal being representative of the amount of the force and thereby being representative of the level of resistance force exerted by the cornea against the blade;
(d) if the force exceeds a predetermined resistance force value, producing an indicating signal indicating that the force exceeds the predetermined resistance force value.

8. The method of claim 7 including producing audible information in response to the indicating signal, step (d) including terminating the incision in response to the audible information.

9. The method of claim 7 including producing graphic information in response to the indicating signal, step (d) including terminating the incision in response to the graphic information.

10. An apparatus for determining the length of an incision in a cornea, comprising in combination:
(a) an RK knife having a blade adapted to extend preselected depth into the cornea;
(b) a transducer connected to the RK knife and producing a first electrical signal representative of force applied to the blade to advance it through the cornea;
(c) an analyzing device receiving the first electrical signal, determining if the amount of force exceeds a predetermined resistance level, and if the amount of force exceeds the predetermined resistance level, producing a second electrical signal indicating that the amount of force exceeds the predetermined resistance level; and
(d) an indicating device adapted to respond to the second electrical signal to produce information indicating that the amount of force exceeds the predetermined resistance level, whereby advancing of the blade in the cornea can be halted in response to the information to thereby establish the length of the incision.

11. The apparatus of claim 10 wherein the transducer engages a body of the RK knife and produces the electrical signal in response to pressure of a surgeon's hand applied against the transducer.

12. The apparatus of claim 10 wherein the indicating device includes a computer adapted to compute the level of the resistance in response to the electrical signal.

13. The apparatus of claim 10 wherein the transducer includes a strain gauge attached to an elongated elastic member supporting the blade.

* * * * *